United States Patent
Nayot et al.

(10) Patent No.: US 10,552,957 B2
(45) Date of Patent: Feb. 4, 2020

(54) METHODS AND SYSTEMS FOR DETERMINING QUALITY OF AN OOCYTE

(71) Applicants: Dan Nayot, Toronto (CA); Rene Michael Bharti, Toronto (CA); Jim Meriano, Mississauga (CA); Alexandr Krivoi, Mississauga (CA)

(72) Inventors: Dan Nayot, Toronto (CA); Rene Michael Bharti, Toronto (CA); Jim Meriano, Mississauga (CA); Alexandr Krivoi, Mississauga (CA)

(*) Notice: Subject to any disclaimer, the term of this patent is extended or adjusted under 35 U.S.C. 154(b) by 0 days.

(21) Appl. No.: 16/362,671

(22) Filed: Mar. 24, 2019

(65) Prior Publication Data
US 2019/0244354 A1    Aug. 8, 2019

Related U.S. Application Data

(60) Provisional application No. 62/647,666, filed on Mar. 24, 2018.

(51) Int. Cl.
*G06K 9/00* (2006.01)
*G06T 7/00* (2017.01)
*G06K 9/46* (2006.01)
*G01N 33/483* (2006.01)

(52) U.S. Cl.
CPC ....... *G06T 7/0014* (2013.01); *G01N 33/4833* (2013.01); *G06K 9/0014* (2013.01); *G06K 9/00134* (2013.01); *G06K 9/46* (2013.01); *G06T 2207/10056* (2013.01); *G06T 2207/20076* (2013.01); *G06T 2207/30024* (2013.01); *G06T 2207/30044* (2013.01)

(58) Field of Classification Search
CPC ........ G06T 7/0014; G06T 2207/10056; G01N 33/4833; G06K 9/00134; G06K 9/0014; G06K 9/46
See application file for complete search history.

(56) References Cited

U.S. PATENT DOCUMENTS

| | | | |
|---|---|---|---|
| 8,265,357 B2* | 9/2012 | Ramsing | G06K 9/00127 345/587 |
| 9,053,353 B2* | 6/2015 | Timmis | A01C 1/00 |
| 9,710,696 B2* | 7/2017 | Wang | G06K 9/6227 |
| 2007/0231784 A1* | 10/2007 | Hoyt | C12N 5/0612 435/4 |
| 2012/0115158 A1* | 5/2012 | Schuchman | C12N 9/80 435/6.18 |
| 2015/0252324 A1* | 9/2015 | Loewke | G01N 33/4833 435/34 |
| 2015/0346100 A1* | 12/2015 | Racowsky | G01N 21/6408 435/34 |
| 2016/0357917 A1* | 12/2016 | Yao | C12Q 1/6809 |
| 2017/0262580 A1* | 9/2017 | Beim | G16B 30/00 |
| 2019/0042958 A1* | 2/2019 | Letterie | G06T 7/13 |

* cited by examiner

*Primary Examiner* — Gregory M Desire
(74) *Attorney, Agent, or Firm* — Bajwa IP Law Firm; Haris Zaheer Bajwa

(57) ABSTRACT

Methods and systems for determining quality of an oocyte to reach various reproductive milestones, including fertilizing, developing into a viable embryo (blastocyst), implanting into the uterus, and reaching a clinical pregnancy, through visual assessment (non-invasive) from a single image using artificial intelligence software.

18 Claims, 7 Drawing Sheets

Dataset egg-fert-crop-clean-v1 - Fertilisation development milestone

*Test Dataset*

```
class  precision   recall   f1-score   support (number of data points)
  0      0.95      0.31      0.46       176
  1      0.89      1.00      0.94       1015 weighted avg       0.90      0.90      0.87       1191

Confusion Matrix:
           pred_neg    pred_pos
true_neg   30.68%      69.32%
true_pos    0.30%      99.70%

Loss = 0.3243728539189187
Accuracy = 0.8950461796809404
AUC = 0.7284090909090908
```

Dataset egg-blast-crop-clean-v1 - Blastocyst development milestone

*Test Dataset*

```
class  precision   recall   f1-score   support (number of data points)
  0      0.68      0.67      0.68       837
  1      0.50      0.52      0.51       541 weighted avg       0.61      0.61      0.61       1378

Confusion Matrix:
           pred_neg    pred_pos
true_neg   67.03%      32.97%
true_pos   48.06%      51.94%

Accuracy = 0.6110304789550073
AUC = 0.6598736354863002
```

FIG. 6

METHODS AND SYSTEMS FOR DETERMINING QUALITY OF AN OOCYTE

PRIORITY

This application claims the benefit of priority from U.S. Provisional Application No. 62/647,666, filed Mar. 24, 2018, entitled "Method and Systems for Determining Quality of an Oocyte," which is hereby incorporated herein by reference in its entirety.

TECHNICAL FIELD

This invention relates to a method and system for determining quality of an oocyte through visual assessment. More specifically the invention relates to utilizing Artificial Intelligence and Cognitive Computing systems to conduct a non-invasive image analysis to determine the reproductive potential of an oocyte, including determining a likelihood that that an oocyte will get fertilized, develop into a embryo (cleavage stage or blastocyst stage), be deemed to be chromosomally normal (euploid), or have the capacity to implant, and become a viable pregnancy.

BACKGROUND

It is well established that women have a reproductive "biological clock", in that egg quality and quantity decreases with advancing age. One method to attempt to overcome the age-related decline in fertility is to preserve oocytes for future use, known as oocyte cryopreservation. When this is done for non-medical reasons, it is referred to as social oocyte cryopreservation.

Although there are currently accepted visual classification systems to grade or evaluate sperm, such as WHO Classification 2010, and embryos, there is no established oocyte classification system that is clinically validated or utilized. Although there are morphological features of an oocyte that can be visualized by light microscopy that have been associated with lower reproductive potential, there is yet to be an integrated classification that can incorporate these features into a validated diagnostic tool. In essence, an egg scoring system or an accurate predictive model is lacking in the field of reproductive medicine.

In patients that undergo oocyte cryopreservation, there is no validated tool that can accurately predict the potential outcomes of each oocyte. Predicting the reproductive outcomes of oocytes is currently performed using historical data based on generally two clinical parameters—the patients age at the time of egg freezing and the total number mature oocytes frozen. This approach (historical data based on age and the number of mature oocytes) is unable provide a genuinely qualitative metric, a scoring method, or criteria for determining likelihood of success for a particular oocyte. No individual oocyte assessment is taken into consideration, so prediction is based on historical data (e.g., twelve eggs in a thirty-three year old patient) instead of personalized data (e.g., assessing the potential of each particular egg). Therefore, there is a need for a visual (non-invasive) oocyte classification system that provides accuracy and serves as tool for embryologists to aid patients in making more sophisticated fertility related decision.

SUMMARY

An object of the invention is to determine quality of an oocyte. Determining quality of the oocyte may refer to the potential of the oocyte to reach various reproductive milestones, including fertilizing, developing into a viable embryo (blastocyst), implanting into the uterus, and reaching a clinical pregnancy, through visual assessment (non-invasive) from a single image using artificial intelligence software. The following presents a simplified summary of exemplary embodiments of the present disclosure in order to provide a basic understanding of some aspects described herein. This summary is not an extensive overview of the claimed subject matter. It is intended to neither identify key nor critical elements of the claimed subject matter nor delineate the scope of the subject innovation. Its sole purpose is to present some concepts of the claimed subject matter.

In an exemplary embodiment, a method for determining quality of an oocyte utilizing artificial intelligence augmented visual assessment through a light microscope. The method may include retrieving from a first database a set of images related to a plurality of oocytes and associated reproductive outcomes including fertilization, blastocyst development, pre-implantation genetic screening (PGS), implantation and clinical pregnancy data, wherein the data indicates binary outcomes of the oocyte (e.g., fertilized or not), wherein there are plurality of images in the set of images associated with each of the plurality of oocytes. The method may further include extracting features from the set of pictures and correlating it, using artificial intelligence, with whether the oocyte was fertilized, reached blastocyst development, was deemed to be PGS normal (euploid), implanted, and resulted in a clinical pregnancy or not. The process may further include receiving an image of a potential oocyte and determining likelihood of it reaching each reproductive milestone based on the extracted features and the image.

This Summary is provided to introduce a selection of concepts in a simplified form; these concepts are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the present disclosure will now be illustrated by way of example. It is expressly understood, however, that the drawings are for the purpose of illustration and description only and are not intended as a definition of the limits of the present disclosure. Embodiments of the present disclosure will now be described by way of example in association with the accompanying drawings in which:

FIGS. 2 C-D show cropped images of oocytes, consistent with one or more exemplary embodiments of the present disclosure;

FIG. 6 illustrates a figure showing results of predictions using exemplary embodiments, consistent with one or more exemplary embodiments.

DETAILED DESCRIPTION

Figure 1:
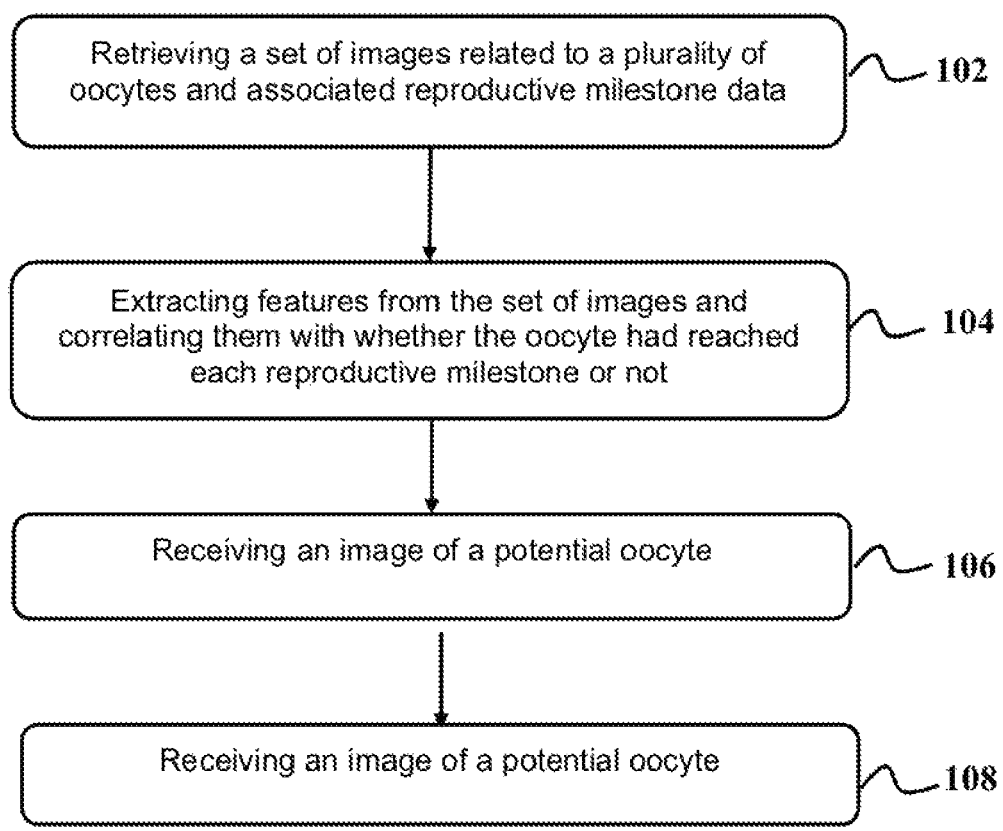
FIG. 1 shows an exemplary method for determining quality of an oocyte, consistent with one or more exemplary embodiments of the present disclosure.

The novel features which are believed to be characteristic of the present invention, as to its structure, organization, use and method of operation, together with further objectives and advantages thereof, will be better understood from the following discussion.

As a preliminary matter, some of the figures describe concepts in the context of one or more structural components, variously referred to as functionality, modules, features, elements, etc. The various components shown in the figures can be implemented in any manner, for example, by software, hardware (e.g., discrete logic components, etc.), firmware, and so on, or any combination of these implementations. In one embodiment, the various components may reflect the use of corresponding components in an actual implementation. In other embodiments, any single component illustrated in the figures may be implemented by a number of actual components. The depiction of any two or more separate components in the figures may reflect different functions performed by a single actual component. The figures discussed below provide details regarding exemplary systems that may be used to implement the disclosed functions.

Some concepts are described in form of steps of a process or method. In this form, certain operations are described as being performed in a certain order. Such implementations are exemplary and non-limiting. Certain operations described herein can be grouped together and performed in a single operation, certain operations can be broken apart into plural component operations, and certain operations can be performed in an order that differs from that which is described herein, including a parallel manner of performing the operations. The operations can be implemented by software, hardware, firmware, manual processing, and the like, or any combination of these implementations. As used herein, hardware may include computer systems, discrete logic components, such as application specific integrated circuits (ASICs) and the like, as well as any combinations thereof.

As to terminology, the phrase "configured to" encompasses any way that any kind of functionality can be constructed to perform an identified operation. The functionality can be configured to perform an operation using, for instance, software, hardware, firmware and the like, or any combinations thereof.

As utilized herein, terms "component," "system," "client" and the like are intended to refer to a computer-related entity, either hardware, software (e.g., in execution), and/or firmware, or a combination thereof. For example, a component can be a process running on a processor, an object, an executable, a program, a function, a library, a subroutine, and/or a computer or a combination of software and hardware.

By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any non-transitory computer-readable device, or media.

Non-transitory computer-readable storage media can include but are not limited to magnetic storage devices (e.g., hard disk, floppy disk, and magnetic strips, among others), optical disks (e.g., compact disk (CD), and digital versatile disk (DVD), among others), smart cards, and flash memory devices (e.g., card, stick, and key drive, among others). In contrast, computer-readable media generally (i.e., not necessarily storage media) may additionally include communication media such as transmission media for wireless signals and the like.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Exemplary methods and systems allow for a single image analysis of the oocyte, and therefore does not require prolonged exposure. That is, exemplary systems and methods provide insight into likelihood of reaching a reproductive milestone based on one singular image of a potential oocyte. Therefore, in an exemplary embodiment, exemplary methods and systems provide a non-invasive, accurate, and fast approach for predicting success rates of potential outcomes of oocytes.

Exemplary application of artificial intelligence to assist with image analysis leads to an exemplary automated and accurate oocyte classification system. The exemplary classification and predictions may serve as a clinically valuable tool in both oocyte cryopreservation cases to help predict the potential outcomes of each oocyte, and in all failed in-vitro fertilization (IVF) cases to better understand the underlying etiology for the lack of success, for example, poor egg quality.

In an exemplary embodiment, for a potential oocyte under consideration, the potential oocyte may be retrieved from an ovarian follicle. The potential oocyte may then be stripped and placed under a light microscope. An exemplary camera mounted on an exemplary light microscope may then capture an image of the stripped oocyte.

In an exemplary embodiment, an object of interest, that is, a potential oocyte or embryo to be evaluated may be identified in the captured image. A captured image may be cropped to isolate the object of interest. Utilizing developed parameters for both processing and analysing images as discussed in further detail below, artificial intelligence may be utilized to determine the likelihood of potential successful outcomes with respect to the potential oocyte or embryo, by utilizing the cropped image focusing on the object of interest. In an exemplary embodiment, an exemplary validation score or prediction may be provided. Additionally, exemplary supportive metrics may be provided, which may include chance of success and confidence in prediction, aiding a clinician in providing advice and guidance to potential patients on medical approaches.

While, the detailed description, focuses on determining quality of an oocyte, analogous exemplary methods may be utilized for additional objects of interest such as embryos.

FIG. 1 shows an exemplary method 100 for determining quality of an oocyte, consistent with one or more exemplary embodiments of the present disclosure. In an exemplary embodiment, determining quality of an oocyte may refer to a metric related to likelihood or potential of an oocyte to fertilize, blastocyst development (develop into a viable embryo), pre-implantation genetic screening (PGS), implantation into the uterus, and clinical pregnancy. Alternatively, it may refer to a prediction regarding whether an oocyte will or will not reach particular reproductive milestones.

Step 102 may include retrieving, from a first database, a set of images related to a plurality of oocytes and associated reproductive milestone data. In an exemplary embodiment, the reproductive milestone data may refer to data related to fertilization, blastocyst development, pre-implantation genetic screening (PGS), implantation, and clinical pregnancy, wherein the data indicates whether the oocyte may have reached a particular reproductive milestone or not. In an exemplary embodiment, a plurality of images associated with each of the plurality of oocytes may be included in the set of images. For example, utilizing time-lapse embryo incubators, a development of a particular oocyte may be monitored through fertilization on to blastocyst, with continuous images. Accordingly, the associated data may indicate whether each reproductive milestone for that particular oocyte was successful or not. For example, fertilization or PGS results (if performed), and whether clinical pregnancy was successful of not. In exemplary embodiments, the data may be parsed so that any influence on the data due to poor sperm quality is minimized.

In an exemplary embodiment, the images may be captured with an image capturing device (not shown) attached to a light microscope (not shown). For example, images may be captured with Hoffman Modulation Contrast optics, at between 250 to 400× magnification.

In an exemplary embodiment, images may be captured in grey scale. In an exemplary embodiment, exposure of an exemplary image capturing device (exemplary camera) may be adjusted in order to capture all details of the subject (for example, oocyte) to be captured. In an exemplary embodiment, the exposure may be adjusted so that no parts of a captured image may be completely black or completely white.

In an exemplary embodiment, all captured images may go through a process of data augmentation, where the images may be transformed by one or more of scaling, rotating, flipping, and adjusting pixel values. In an exemplary embodiment, data augmentation may allow for standardization of the all the captured images. In an exemplary embodiment, standardizing all the captured images to user defined or automatically generated parameters may be valuable in terms of improving predictive accuracy.

In an exemplary embodiment, creating a clean and unbiased dataset may serve as a critical part of developing a robust predictive model. A clean and unbiased data set may refer to both image quality and data linking, that is, an accurate record of images and reproductive outcomes. In an exemplary embodiment, any images with undesirable qualities such as debris, shadowing, poor exposure, etc., may be removed from respective datasets.

As discussed above, the first set of data may include images of oocytes and their respective reproductive milestone outcomes. The outcome of each oocyte used in an exemplary dataset may be accounted for, from fertilization to embryo transfer, thus producing a clean dataset. A large pool of oocyte images may be retrieved from time-lapse incubator videos. The first image of the time-lapse incubator video may represent a stripped mature oocyte within a few minutes after being injected with a single sperm (ICSI—intracytoplasmic sperm injection). The time-lapse incubator video traditionally may have sequential images from the oocyte to a blastocyst (Day 5 or 6 of embryo development).

Another set of data may include captured single images of mature oocytes (after stripping, but before ICSI) using a camera mounted on a light microscope and may be correlated with the image of the same oocyte (after ICSI) within the time-lapse incubator (first image of the time-lapse video). This exemplary data set may be utilized below with respect to step 104 to develop and/or train predictive model trained on first images of the oocytes within the time-lapse incubator to recognize and predict outcomes on single image of a pre-ICSI mature oocyte under a light microscope.

In an exemplary embodiment, captured images may have a 300× magnification. Resolution of the source image before cropping may be 3000 by 3000 pixels with a potential oocyte included within the image.

FIGS. 2 A-B illustrate images of oocytes captured by a microscope, consistent with one or more exemplary embodiments of the present disclosure. Specifically, FIG. 2A shows a mature oocyte (after stripping) which is held in place with suction before Intracytoplasmic sperm injection (ICSI) is performed. FIG. 2B shows a first image of another oocyte from a time-lapse incubator.

In an exemplary embodiment, the captured image may be cropped with the object of interest (oocyte) in the center. For example, an image may be cropped to a resolution of 230 by 230 pixels with a potential oocyte in the center of the cropped image. An image may be cropped around the oocyte, since the oocyte's shape is mostly round, a potential oocyte appears in the center of a cropped image. In an exemplary embodiment, a size of the cropped image may depend on the magnification of the lens on the microscope and resolution of the camera. In an exemplary embodiment, an image of an object of interest (for example, an oocyte) may be at least 230 by 230 pixels after cropping.

Figure 2A:
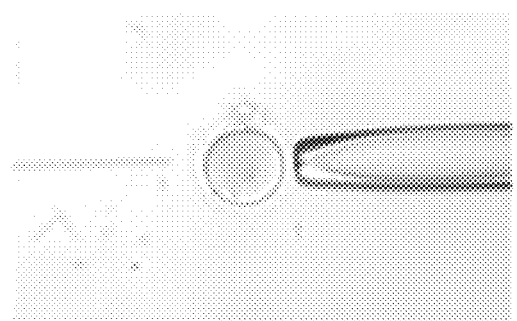
FIGS. 2 A-B illustrate images of oocytes captured by a microscope, consistent with one or more exemplary embodiments of the present disclosure.
Figure 2B:
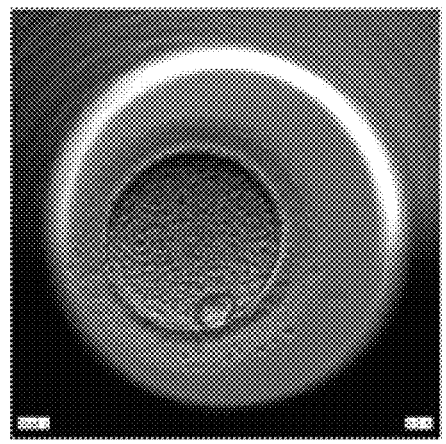
Figure 2C:
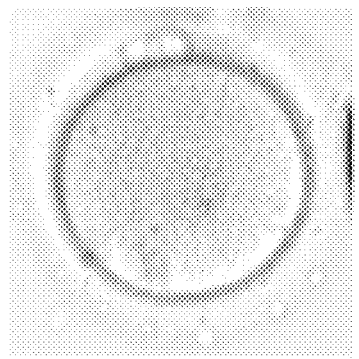
Figure 2D:
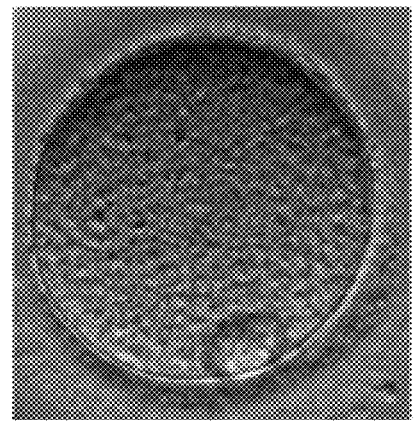

FIGS. 2C-D shows cropped images of oocytes, consistent with one or more exemplary embodiments of the present disclosure. Specifically, FIG. 2C shows the image presented in FIG. 2A cropped with the oocyte in the center. Similarly, FIG. 2D shows the first image of FIG. 2B cropped with the oocyte in the center.

Step 104 may include extracting features from the set of images and correlating it, using artificial intelligence, with whether the oocyte had reached each reproductive milestone (described above) or not. In exemplary embodiments, artificial intelligence may refer to a software platform and computing system capable of analyzing image data. The exemplary platform may include elements of Cognitive Computing and Machine Learning. In exemplary embodiments, AI may be used for processes related to exemplary embodiments including utilizing as a Oocyte Feature Analysis system for the extracting and matching of features indicating likelihood of fertilization, blastocyst development, PGS implantation, and clinical pregnancy, and as a Cognitive computing system required to machine learn from a vast store of data, and as an Analytics system to enabling data modeling and predictive data modeling for future states. Accordingly, using artificial intelligence features may be extracted which indicated a higher likelihood of fertilization, blastocyst development, PGS, implantation, and clinical pregnancy Step 106 may include receiving an image of a potential oocyte. For example, an image of a patient's sample oocyte may be taken to determine its likelihood of reaching each of the reproductive milestones. The patient's sample oocyte may also be referred to as a potential oocyte, that is, a potential oocyte which may be used in a reproductive process. In an exemplary embodiment, a clinician or a physician may be tasked with capturing an image of a potential oocyte. The captured image may be uploaded to a cloud environment or transferred to a computing system using a network or other methods. In an exemplary embodiment, an image of a potential oocyte may be captured utilizing an image capturing device, such as a camera, attached to a light microscope.

Figure 3:
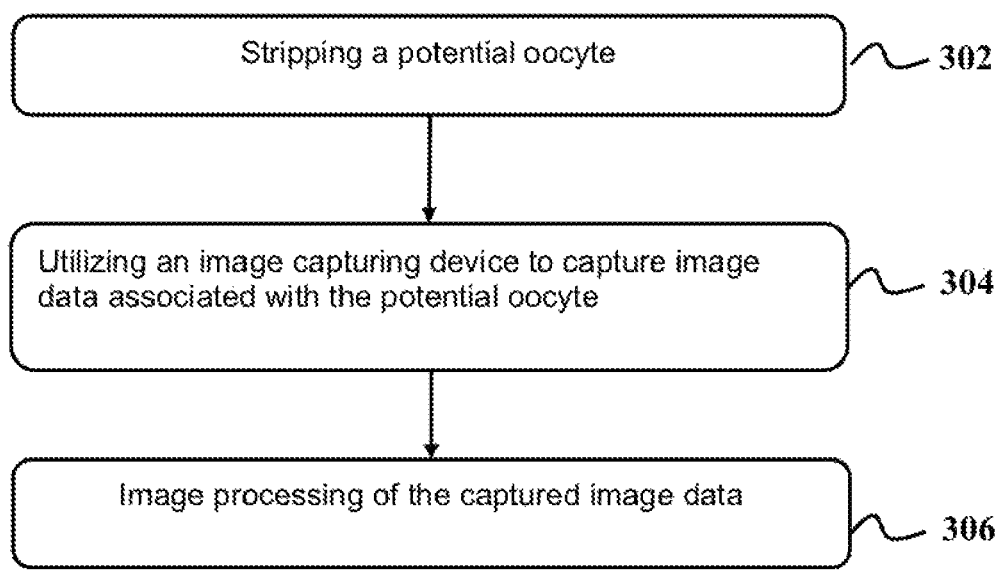
FIG. 3 illustrates a process for capturing an image of a potential oocyte, consistent with one or more exemplary embodiment of the present disclosure.

FIG. 3 illustrates a process for capturing an image of a potential oocyte, consistent with one or more exemplary embodiment of the present disclosure.

Step 302 may comprise stripping a potential oocyte. In an exemplary embodiment, stripping may refer to separating the potential oocyte from other surrounding cells. This may be done under an exemplary high-power microscope, such as an ICSI microscope. In an exemplary embodiment, before stripping the potential oocyte, it may be retrieved from an ovarian follicle.

Step 304 may comprise utilizing an image capturing device to capture image data associated with the potential oocyte. In an exemplary embodiment, the image of the potential oocyte may be captured after stripping and immediately pre-ICSI or pre-freezing.

In an exemplary embodiment, settings and/or conditions for capturing an image of a potential oocyte may be the same as the previously captured images referred to in step 102 which were captured from a light microscope. For example, a camera attached to an exemplary high-power microscope may be used to capture the image of a potential oocyte. For example, images may be captured with Hoffman Modulation Contrast optics, at between 250 to 400× magnification. In an exemplary embodiment, images may be captured in grey scale. In an exemplary embodiment, exposure of an exemplary camera may be adjusted in order to capture all details of the subject to be captured. In an exemplary embodiment, the exposure may be adjusted so that all parts of the potential object to be evaluated are clear.

Step 306 may comprise image processing of the captured image data. Image processing of the captured image data may comprise cropping the captured image data so that the potential oocyte is in the center and/or applying above-mentioned process of data augmentation. In an exemplary embodiment, the captured image may be cropped with the object of interest in the center. In an exemplary embodiment, an image of an object of interest (for example, a potential oocyte) may be at least 230 by 230 pixels after cropping. An image may be cropped around the oocyte, since the oocyte's shape is mostly round, the potential oocyte appears in the center of an image. In an exemplary embodiment, a size of the cropped image may depend on the magnification of the lens on the microscope and resolution of the camera.

In an exemplary embodiment, capturing an image of an object of interest, such as a potential oocyte may be conducted in similar manner and specification as capturing of the training data sets. In an exemplary embodiment, this may allow for more efficiency and accuracy in predictive accuracy of exemplary systems.

Figure 4:
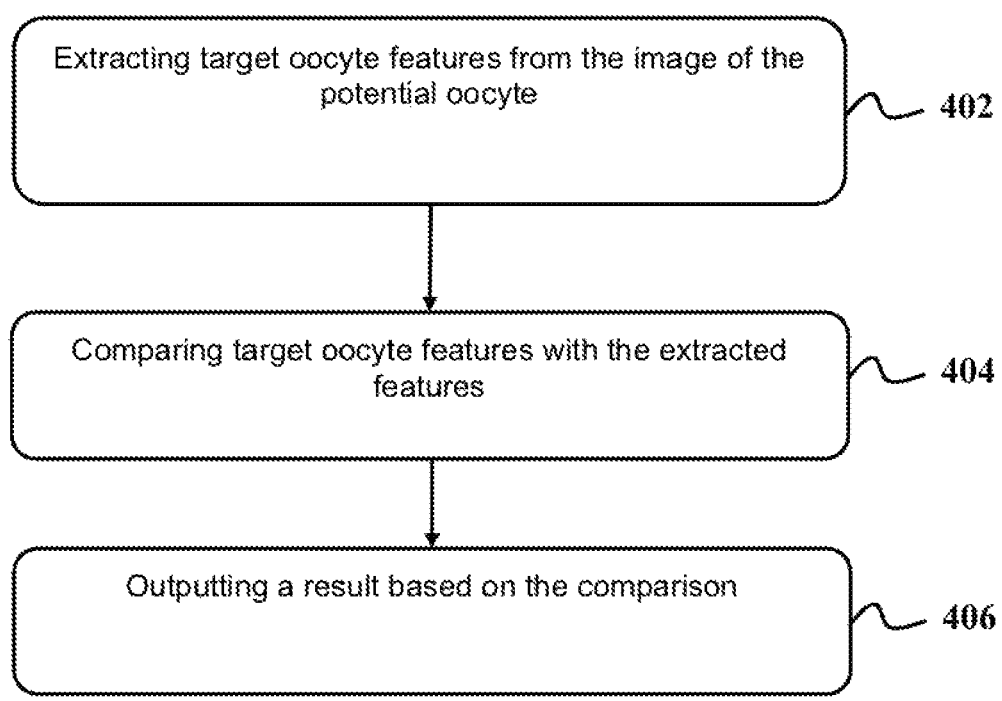
FIG. 4 illustrates an exemplary process for determining likelihood of reaching each of the reproductive milestones of the potential oocyte based on the extracted features and the image, consistent with one or more exemplary embodiments of the present disclosure.

Step 108 may include determining likelihood of reaching each of the reproductive milestones of the potential oocyte based on the extracted features and the image. Specifically, a likelihood in terms of percentage, a ranking, or a numerical value may be calculated for fertilization, blastocyst development, PGS (pre-implantation genetic screening), implantation, and clinical pregnancy. In an exemplary embodiment, a simple prediction regarding each reproductive milestone may be made. In an exemplary embodiment, method 400 illustrates the details of Step 108 in FIG. 4, consistent with exemplary embodiments of the present disclosure. Specifically, step 402 may include extracting target oocyte features from the image of the potential oocyte. For example, based on extracted features of sample oocyte images, it may be determined what features indicate likelihood of reproductive milestones, such as fertilization, or lack thereof. For example, target oocyte features which may indicate likelihood of fertilization in a positive or negative way may be extracted.

Step 404 may include comparing target oocyte features with the extracted features. Specifically, the features extracted utilizing artificial intelligence (for example utilizing exemplary step 104 above) may be compared with the target object of interest features, such as oocyte features.

Step 406 may include outputting a result based on the comparison. For example, if the potential oocyte contains features which correlate with likelihood of each reproductive milestone (described above) or lack thereof, the results may be output.

In an exemplary embodiment, analogous methods as discussed above with respect to methods 100, 300, and 400 with regards to oocyte quality and predicting likelihood of fertilization, blastocyst development, PGS, implantation and clinical pregnancy may be used for numerous other processes. For example, analogous exemplary methods may be utilized for sperm assessment (that is, select the best potential sperm to fertilize an egg with), embryo assessment, and uterine cavity assessment.

Figure 5:
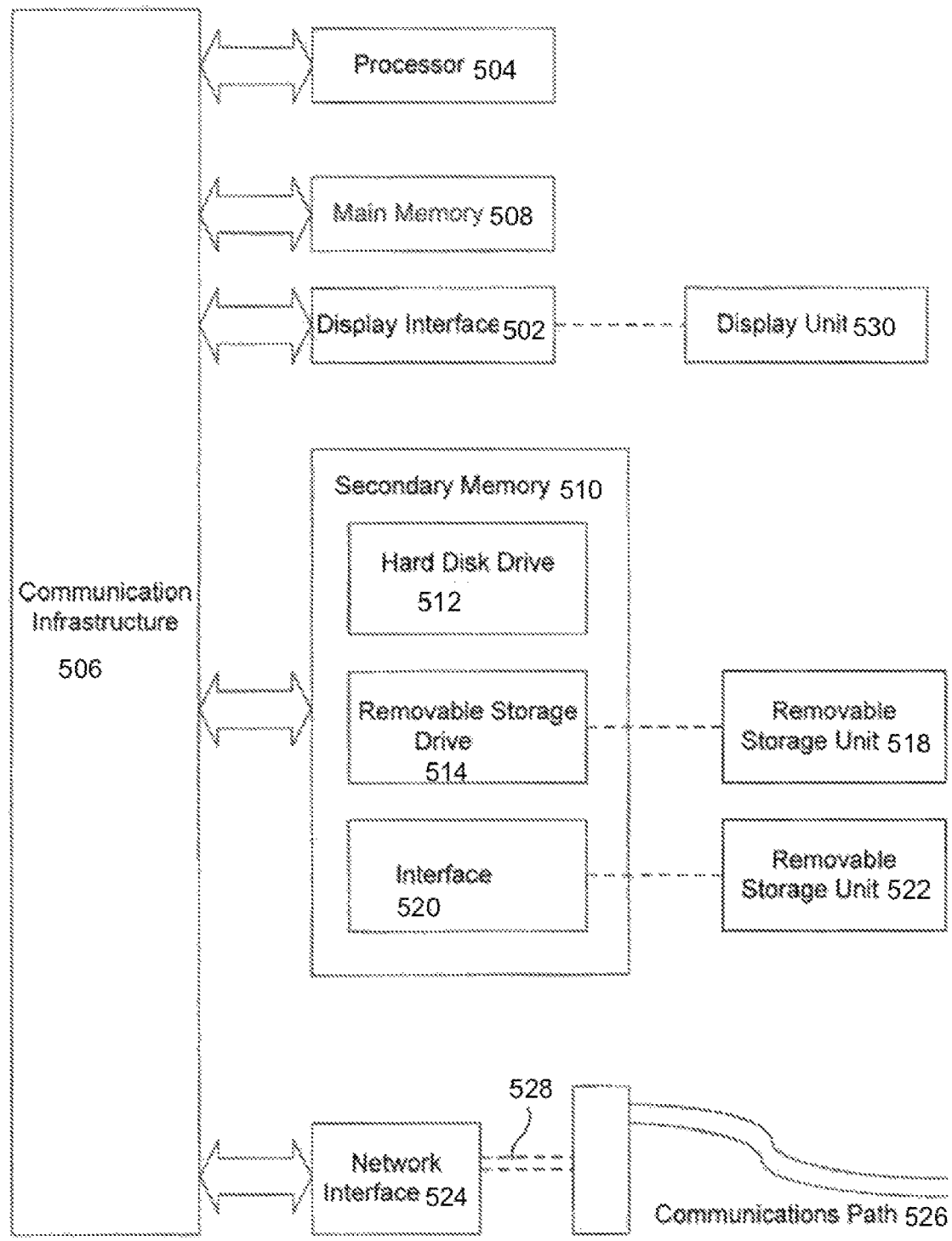
FIG. 5 illustrates an example computer system in which an embodiment of the present invention, or portions thereof, may be implemented as computer-readable code, consistent with exemplary embodiments of the present disclosure.

FIG. 5 illustrates an example computer system 500 in which an embodiment of the present invention, or portions thereof, may be implemented as computer-readable code, consistent with exemplary embodiments of the present disclosure. For example, device 100 may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components utilized with respect to the methods described in FIGS. 1, 3, and 4.

Digital camera attached to a port on the light microscope and to a computer system via USB/Ethernet cable or other means. Application that allows operator to take a picture when oocyte is ready to be captured. Application that performs analysis and displays prediction result.

If programmable logic is used, such logic may execute on a commercially available processing platform or a special purpose device. One of ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 is connected to a communication infrastructure 506, for example, a bus, message queue, network, or multi-core message-passing scheme.

Computer system 500 also includes a main memory 508, for example, random access memory (RAM), and may also include a secondary memory 510. Secondary memory 510 may include, for example, a hard disk drive 512, removable storage drive 514. Removable storage drive 514 may comprise a floppy disk drive, a magnetic tape drive, an optical disk drive, a flash memory, or the like. The removable storage drive 514 reads from and/or writes to a removable storage unit 518 in a well-known manner. Removable storage unit 518 may comprise a floppy disk, magnetic tape, optical disk, etc., which is read by and written to by removable storage drive 514. As will be appreciated by persons skilled in the relevant art, removable storage unit 518 includes a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from the removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement the present invention as discussed herein. In particular, the computer programs, when executed, enable processor device 504 to implement the processes of the present invention, such as the operations in the method illustrated by flowchart 100 of FIG. 1, flowchart 300 of FIG. 3, and flowchart 400 of FIG. 4 discussed above. Accordingly, such computer programs represent controllers of the computer system 500. Where the invention is implemented using software, the software may be stored in a computer program product and loaded into computer system 500 using removable storage drive 514, interface 520, and hard disk drive 512, or communications interface 524.

Embodiments of the invention also may be directed to computer program products comprising software stored on any computer useable medium. Such software, when executed in one or more data processing device, causes a data processing device(s) to operate as described herein. An embodiment of the invention employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

EXAMPLES

In an exemplary embodiment, FIG. 6 illustrates a figure showing results of predictions using exemplary embodiments, consistent with one or more exemplary embodiments. As may be seen, in fertilization stage testing utilizing verified data, when it was predicted that a result, with respect to fertilization would be positive, it was a true positive in 99.70 percent of the cases. Similarly, when it was predicted that a result would be negative using exemplary systems and methods, the results were a true positive in only 0.30 percent of the cases. Essentially, utilizing exemplary systems and methods leads to higher chance of a successful pregnancy, as predicted negatives tend to lead to true negatives so such potential oocytes may be eliminated from consideration. As may be seen, the overall accuracy is 89.5 percent to determine likelihood of fertilization utilizing exemplary methods and exemplary systems.

Similarly, with respect to determining likelihood of blastocyst, when a negative is predicted, it is more likely than not that the negative prediction is accurate. Accordingly, overall likelihood is increased if a clinician only chooses to utilize oocytes which are positively predicted to meet a reproductive milestone.

In an exemplary embodiment, exemplary methods described above may be utilized to predict both fertilization, blastocyst development, and clinical pregnancy.

In an exemplary embodiment, analogous methods described above may be utilized to evaluate eggs, embryos, and endometrial cavity.

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed:

1. A method for determining quality of an oocyte, comprising:
   retrieving, from one or more databases, a set of images related to a plurality of oocytes and associated reproductive milestone data, wherein the fertilization data indicates whether the oocyte was fertilized or not, wherein there are plurality of images in the set of images associated with each of the plurality of oocytes;
   extracting features from the set of images and correlating the features, using artificial intelligence, with whether the oocyte was fertilized or not;
   receiving an image of a potential oocyte; and
   determining, using one or more processors, likelihood of reaching each of the reproductive milestones of the potential oocyte based on the extracted features and the image of the potential oocyte, wherein determining likelihood of fertilization comprises:
      extracting target oocyte features from the image of the potential oocyte;
      comparing target oocyte features with the extracted features; and
      outputting a result based on the comparison and the correlation.

2. The method of claim 1, wherein determining likelihood of reaching each of the reproductive milestones of the potential oocyte comprises determining likelihood of one of fertilization, blastocyst development, detection of birth defect in Preimplanation Genetic Screen, implantation, and clinical pregnancy.

3. The method of claim 1, further comprising:
   capturing the image of the potential oocyte, comprising:
      stripping the potential oocyte from other surrounding cells;
      utilizing an image capturing device to capture image data associated with the potential oocyte; and
      image processing of the captured image data.

4. The method of claim 3, wherein image processing of the captured image data comprises generating a cropped image by cropping the captured image data so that the potential oocyte is in a center of the cropped image.

5. The method of claim 4, wherein generating the cropped image comprises generating the cropped image with a resolution of at least 230 by 230 pixels.

6. The method of claim 3, wherein utilizing the image capturing device to capture the image data associated with the potential oocyte comprises utilizing the image capturing device to capture image data in grey scale with a magnification of at least 250×.

7. The method of claim 3, wherein utilizing the image capturing device to capture the image data associated with the potential oocyte comprises utilizing the image capturing device to capture the image data before Intracytoplasmic sperm injection or freezing of the oocyte.

8. The method of claim 1, wherein determining likelihood of reaching each of the reproductive milestones of the potential oocyte comprises determining likelihood of fertilization.

9. The method of claim 1, wherein determining receiving the image of a potential oocyte comprises receiving only a singular image of the potential oocyte.

10. A system for method for determining quality of an oocyte, the system comprising:
    one or more processors; and
    a storage device that stores a set of instructions that when executed by the one or more processors perform a method, the method comprising:
       retrieving, from one or more databases, a set of images related to a plurality of oocytes and associated reproductive milestone data, wherein the fertilization data indicates whether the oocyte was fertilized or not, wherein there are plurality of images in the set of images associated with each of the plurality of oocytes;
       extracting features from the set of images and correlating the features, using artificial intelligence, with whether the oocyte was fertilized or not;
       receiving an image of a potential oocyte; and
       determining likelihood of reaching each of the reproductive milestones of the potential oocyte based on the extracted features and the image of the potential oocyte, wherein determining likelihood of fertilization comprises:
          extracting target oocyte features from the image of the potential oocyte;
          comparing target oocyte features with the extracted features; and
          outputting a result based on the comparison and the correlation.

11. The system of claim 10, wherein determining likelihood of reaching each of the reproductive milestones of the potential oocyte comprises determining likelihood of one of fertilization, blastocyst development, detection of birth defect in Preimplanation Genetic Screen, implantation, and clinical pregnancy.

12. The system of claim 10, wherein the method further comprising:
- capturing the image of the potential oocyte, comprising:
  - stripping the potential oocyte from other surrounding cells;
  - utilizing an image capturing device to capture image data associated with the potential oocyte; and
- image processing of the captured image data.

13. The system of claim 12, wherein image processing of the captured image data comprises generating a cropped image by cropping the captured image data so that the potential oocyte is in a center of the cropped image.

14. The system of claim 13, wherein generating the cropped image comprises generating the cropped image with a resolution of at least 230 by 230 pixels.

15. The system of claim 14, wherein utilizing the image capturing device to capture the image data associated with the potential oocyte comprises utilizing the image capturing device to capture image data in grey scale with a magnification of at least 250×.

16. The system of claim 14, wherein utilizing the image capturing device to capture the image data associated with the potential oocyte comprises utilizing the image capturing device to capture the image data before Intracytoplasmic sperm injection or freezing of the oocyte.

17. The system of claim 10, wherein determining likelihood of reaching each of the reproductive milestones of the potential oocyte comprises determining likelihood of fertilization.

18. The system of claim 10, wherein determining receiving the image of a potential oocyte comprises receiving only a singular image of the potential oocyte.

* * * * *